United States Patent [19]

Valentini et al.

[11] 4,069,819
[45] Jan. 24, 1978

[54] INHALATION DEVICE

[75] Inventors: Luigi Valentini; Michele Maiorano, both of Milan, Italy

[73] Assignee: Societa Farmaceutici S.p.A., Milan, Italy

[21] Appl. No.: 711,962

[22] Filed: Aug. 5, 1976

Related U.S. Application Data

[63] Continuation of Ser. No. 576,204, May 9, 1975, abandoned, which is a continuation of Ser. No. 414,214, Nov. 9, 1973, abandoned.

[30] Foreign Application Priority Data

Apr. 13, 1973  Italy ................................. 22968/73

[51] Int. Cl.² ............................................. A61M 15/08
[52] U.S. Cl. .................................... 128/206; 128/208; 128/266
[58] Field of Search ............... 128/266, 205, 206, 208, 128/265, 173 H; 222/193

[56] References Cited

U.S. PATENT DOCUMENTS

| | | | |
|---|---|---|---|
| 3,635,219 | 1/1972 | Altounyan et al. | 128/208 |
| 3,795,244 | 3/1974 | Lax et al. | 128/208 |
| 3,807,400 | 4/1974 | Cocozza | 128/208 |
| 3,906,950 | 9/1975 | Cocozza | 128/266 |

Primary Examiner—Robert W. Michell
Assistant Examiner—Henry J. Recla
Attorney, Agent, or Firm—Stevens, Davis, Miller & Mosher

[57] ABSTRACT

An inhalation device of cylindrical form is disclosed for the administration of medicaments in finely divided form, having a nebulization chamber for a capsule with the medicament and in which an air passageway is formed in such manner as to set the flowing air in vortical motion. The vortical motion is obtained by means of holes suitably directed or by other means such as inclined surfaces, helicoidal parts or the like. The nebulization chamber is such as to cause the capsule, under the action of the flowing air, to make movements of rotation, procession and vibration about and along its longitudinal axis within the nebulization chamber. A series of air inlet holes may be provided in the periphery of the lower portion of the nebulization chamber, the axes of which are offset from the central axis of the nebulization chamber. One or more push button-actuated needles pierce the capsule and release the powdered medicament.

5 Claims, 6 Drawing Figures

U.S. Patent  Jan. 24, 1978  Sheet 1 of 2  4,069,819
FIG. 1
FIG. 2
FIG. 4
FIG. 3
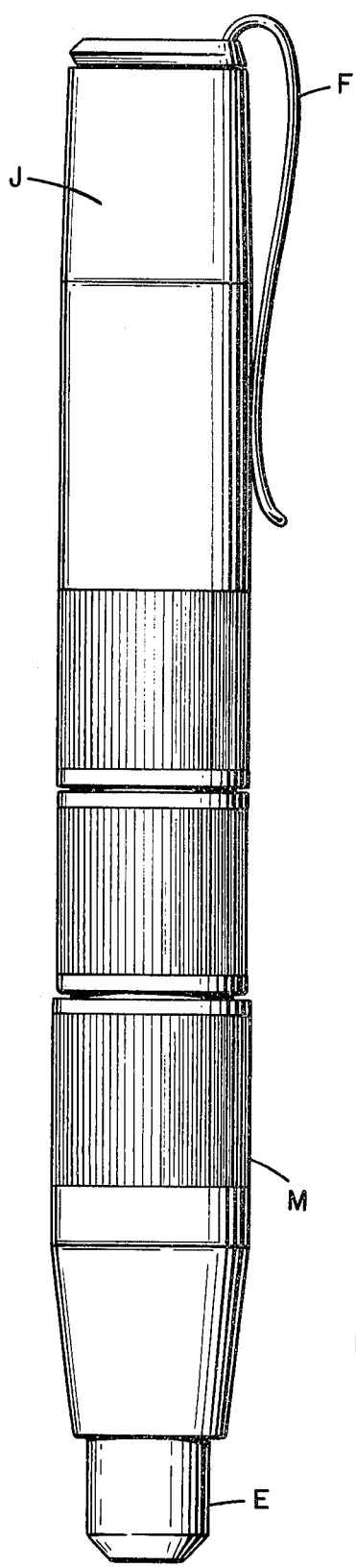
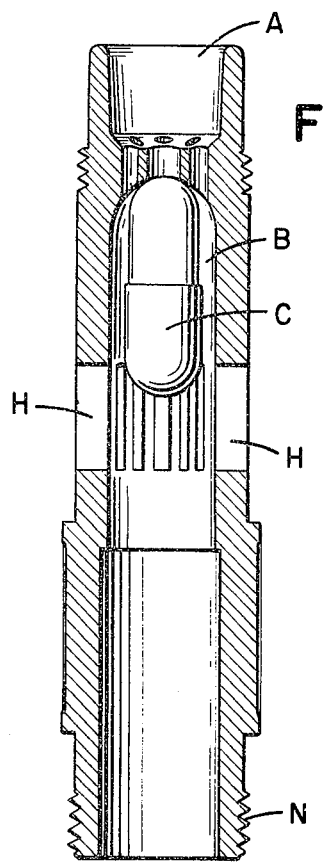
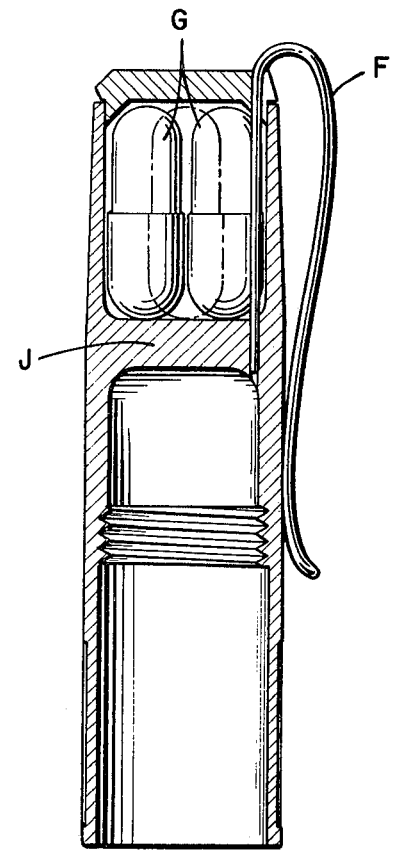
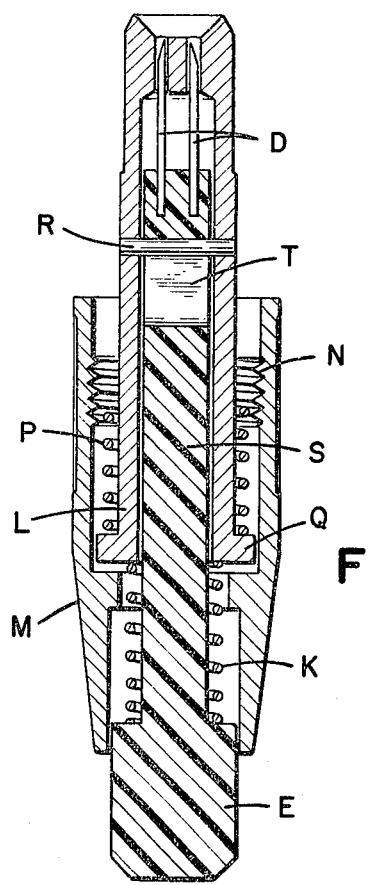

INHALATION DEVICE

This is a Continuation of application Ser. No. 576,204 filed May 9, 1975 now abandoned, which in turn is a continuation of application Ser. No. 414,214, filed Nov. 9, 1973 and now abandoned.

The present invention relates to a device for the administration of medicaments in finely divided form, by oral inhalation.

Many devices for the administration of medicaments in finely divided form have been previously described (e.g., British Pat. No. 1,182,779; U.S. Pat. No. 3,635,219). Each, however, is limited with regard to the movement of the capsule of the device in its housing under the action of air. In particular, in the prior art devices the ejection of the powder from the capsule depends almost exclusively on its rotatory motion around its axis and this involves the disadvantage of an irregularity of ejection in time space.

It is an object of the present invention to overcome the above and other disadvantages. For the purpose, the capsule of the device is so constructed and arranged that it is subject to three movements: rotation, precession and vibration. This allows a regular and complete nebulization of the powdered medicament.

More particularly, the present invention comprises an inhalation device of cylindrical form, having at one end a nebulization chamber inside of which is placed the capsule containing the powdered medicament. The passageway for the air is made in such manner as to set the air itself in vortical motion. This may be achieved either by means of holes or passageways suitably oriented, or by means of other elements such as inclined surfaces, helicoidal parts or the like.

The nebulization chamber is of course larger in cross-section than the capsule and has such a form that the entrance of air thereto during inspiration, with a vortical movement, imparts the aforesaid movements of rotation, precession and vibration to the capsule which is loosely held within the nebulization chamber. These movements bring about the regular and total release of the powdered medicament. The quantitative relationship of these three movements is determined by the shape of the chamber.

At the other end of the inhalation device a pushbutton is provided which upon pressing causes one or more needles, generally three, to press against the capsule, causing perforation of the capsule. The powdered medicament comes out of these holes and then is dispersed in the air.

The end of the inhalation device which is adapted for inspiration is protected by a cap provided with a clip, and within which there is a cavity for holding a number (e.g., three) spare capsules. The capsules containing the powdered medicament are made of a material readily perforable by the needles, gelatine being a preferred example of such a material.

The inhalation device is simple to use and is of relatively slight bulk and therefore one of minimum encumbrance. It can be carried in the pocket as a pen, which it resembles, and the cap prevents external contamination. In use, one merely takes off the cap, brings the device to the nose or mouth, presses the push-button, and inspires.

In order still further to explain the device as regards its form and its way of working, reference is made to the accompanying drawings, wherein:

FIG. 1 represents the whole inhalation device in a static position.

FIG. 2 is a section through the upper end of the device in FIG. 1 with the cap removed.

FIG. 3 is a section through a lower end of the device in FIG. 1.

FIG. 4 is a section through a cap at the upper end of the device in FIG. 1.

Figure 5:
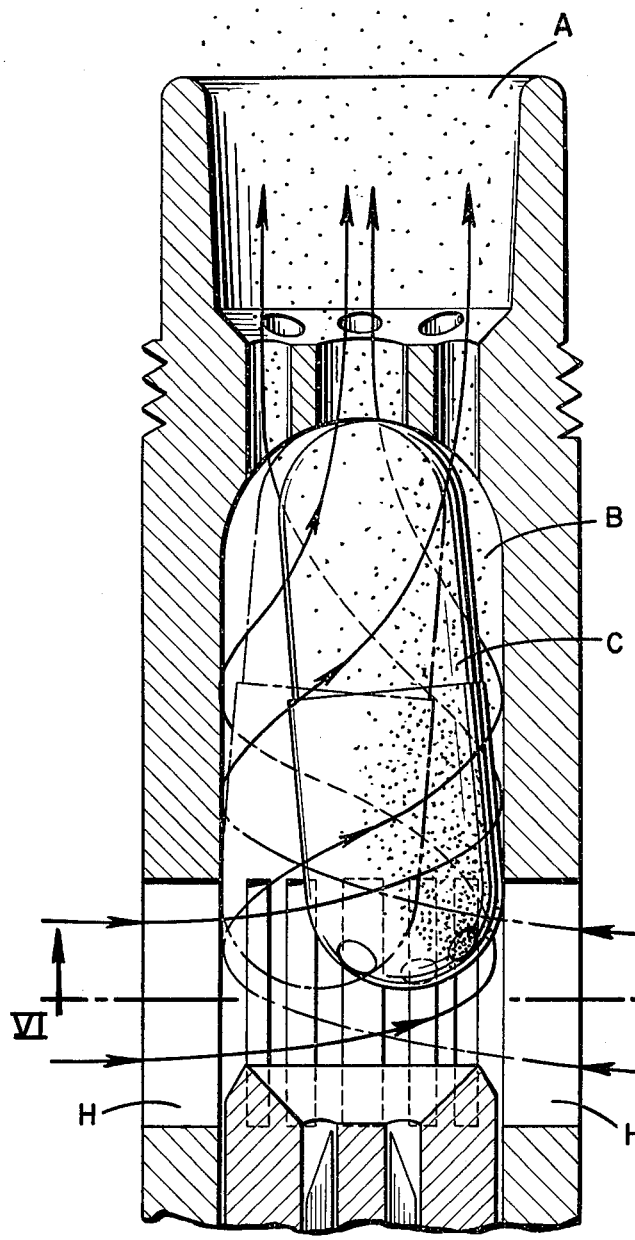
FIG. 5 shows on a larger scale a nebulization chamber in FIG. 2.
Figure 6:
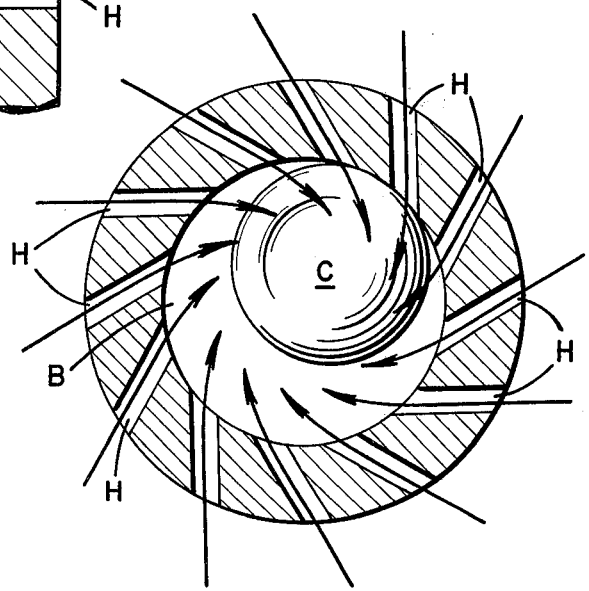
FIG. 6 is a section on VI — VI of FIG. 5.

With reference to the drawings, an inhalation device comprises a nebulization chamber B (FIGS. 2 and 5) shown as containing a capsule C of finely divided medicament. The chamber B is provided with a number of passageways H for the admission of air. The chamber B and passageways H are so arranged, as to the internal shape of the chamber B in relation to the capsule C and the orientation, direction and dimensions of the passageways H, that on inhalation air drawn in through the passageways H is put in a vortical motion, thus subjecting the capsule C to rotary, precessional and vibratory motion.

The inhalation device has at the upper end an inspiration opening A (FIGS. 2 and 5) which is applied to the nose or mouth for inhalation. For carrying purposes, the inhalation device is provided with a cap J (FIGS. 1 and 4) screw-threaded over the inspiration opening A. The cap J is provided with a pocket clip F and a cavity for up to three spare capsules G.

At the lower end is a push-button E (FIGS. 1 and 3) for driving three needles D into the capsule C to liberate medicament. The push-button E is integral with a shaft S from the top of which project the needles D. Near the top of the shaft S, a short relatively narrow slot T is provided that extends all the way through the shaft.

A lower generally hollow cylindrical part L of the inhalation device is pierced by two holes into which a peg R is inserted in tight press-fit engagement. The peg R is of such a length that its ends are flush with the outer circumference of that portion of the outer diameter of the hollow cylindrical part into which it fits, and the diameter of the peg R is slightly less than the thickness of the slot T so that it can slide freely up and down within the slot.

The needles D extend into, and can be pushed upwardly through, matching holes provided near the upper end of the lower part L. The lower part L surrounds the upper part of the shaft S with sufficient clearance between the two so as to permit free movement between the two in an axial direction; a movement the maximum extent of which is predetermined by the length of the slot T.

The push-button E is loaded by a coil spring K bearing on the lower part L of the inhalation device for the withdrawal of the needles D after perforation of the capsule C. The lower part L fits inside the lower end of the upper part of the device shown in FIG. 2, and is secured therein by a cover M, which engages the upper part through screw threads N, and by a coil spring P which bears on the lower end of the upper part of the device and on a shoulder Q on the lower end of the lower part L.

Upon actuation by pressure of the finger of the user on push-button E, both the shaft S and the lower part L are first pushed upwardly until the upper part of L engages the capsule C in the chamber B. Further pressure on push button E causes the shaft S carrying the needles D to continue upwardly to the extent permitted by the slot T while L remains stationary. This causes the needles D to perforate the capsule C. On releasing the push-button E, the withdrawal spring K returns the push-button E and associated parts to the carrying position and thus removes the needles D from the capsule C. The inhalation device can then be used by placing the inspiration opening A in the nose or mouth and inspiring.

Air is thus drawn in through the passageways H, and given a vortical movement thereby. The capsule C is thus subjected to a rotary, precessional and vibratory movement, and the medicament contained in the capsule is thus used up regularly, and eventually completely.

What is claimed is:

1. A pen-shaped pocket-size inhalation device of relative slight bulk and of elongated generally cylindrical form for the administration upon inhalation via a persons' nose or mouth of a medicament in finely-divided form contained within a capsule disposed in the interior of the device, said device including a generally cylindrical wall structure having a centrally unobstructed axially-extending nebulization chamber adapted to contain said capsule, said nebulization chamber having dimensions slightly larger than, and adapted to loosely hold, a capsule of smaller dimensions containing mediament therein in substantially axial position with respect to said nebulization chamber said device having air passage means extending through said wall structure adjacent one end of said nebulization chamber for the flow of air through said wall structure and into said nebulization chamber for setting in vortical motion air flowing through the device solely by inhalation, thereby causing the loosely held capsule disposed within the slightly larger nebulization chamber, under the action of the flowing air, to make random movements of rotation, precession and vibration about and along its longitudinal axis while loosely held and freely movable within the nebulization chamber, unitary spring-biased means including at least one capsule-perforating needle disposed at one end of said cylindrical structure and in an axially retracted manner with respect to said cylindrical structure, said needle disposed adjacent one end of the nebulization chamber and including means actuatable manually by the person whereby the end of the capsule may be readily perforated for release of the contained medicament into the air flowing with a vortical motion through the nebulization chamber and at least one discharge hole in said cylindrical structure communicating with the nebulization chamber at the opposite end thereof for releasing finely-divided medicament dispersed in the air from the nebulization chamber into the person's nose or mouth.

2. An inhalation device according to claim 1, wherein the vortical motion of the air is obtained by means of a plurality of openings in the wall of the nebulization chamber.

3. An inhalation device according to claim 2, wherein the side wall of the nebulization chamber is provided with a plurality of air inlet openings located about the periphery thereof, the axes of the openings in the plane perpendicular to the central axis of the nebulization chamber being offset from said central axis, thereby bringing about the said vortical flow of air through said nebulization chamber.

4. An inhalation device according to claim 1, including a spring-loaded pushbutton located in the end thereof opposite the nebulization chamber, and slidably disposed in said device so that upon pressing said pushbutton, one or more needles fixedly associated with the pushbutton are moved against and into the finely-divided medicament-containing capsule disposed within the nebulization chamber, causing perforation of the capsule and from the holes thus obtained, releasing from the capsule the finely-divided medicament which is then dispersed in the vortically flowing air by which the finely-divided medicament is introduced into the person's nose or mouth.

5. An inhalation device according to claim 1, including a cap for same provided with a chamber having a cavity adapted to contain spare finely-divided medicament-containing capsules.

* * * * *

UNITED STATES PATENT AND TRADEMARK OFFICE
CERTIFICATE OF CORRECTION

PATENT NO. : 4,069,819
DATED : January 24, 1978
INVENTOR(S) : Luigi VALENTINI et al It is certified that error appears in the above-identified patent and that said Letters Patent are hereby corrected as shown below:

In the Abstract, line 11, correct "procession" to read --precession--;

Column 1, line 63, after "cap," insert --presses the push-button,--;

Column 1, line 64, after "mouth," delete --presses the push-button,--;

Please correct Figure 3 as indicated by the red lines on the attached drawings.

Signed and Sealed this

Twenty-sixth Day of September 1978

[SEAL]

Attest:

RUTH C. MASON
Attesting Officer

DONALD W. BANNER
Commissioner of Patents and Trademarks